(12) United States Patent
Denham

(10) Patent No.: US 10,292,824 B2
(45) Date of Patent: May 21, 2019

(54) LABRAL RECONSTRUCTION SYSTEM AND METHODS

(71) Applicant: Biomet Sports Medicine, LLC, Warsaw, IN (US)

(72) Inventor: Gregory J. Denham, Warsaw, IN (US)

(73) Assignee: Biomet Sports Medicine, LLC, Warsaw, IN (US)

( * ) Notice: Subject to any disclaimer, the term of this patent is extended or adjusted under 35 U.S.C. 154(b) by 81 days.

(21) Appl. No.: 15/346,059

(22) Filed: Nov. 8, 2016

(65) Prior Publication Data

US 2017/0128215 A1    May 11, 2017

Related U.S. Application Data

(60) Provisional application No. 62/253,431, filed on Nov. 10, 2015.

(51) Int. Cl.
*A61F 2/34* (2006.01)
*A61F 2/40* (2006.01)
*A61F 2/30* (2006.01)

(52) U.S. Cl.
CPC ........ *A61F 2/30756* (2013.01); *A61F 2/3094* (2013.01); *A61F 2/4081* (2013.01); *A61F 2/34* (2013.01); *A61F 2002/30293* (2013.01); *A61F 2002/30461* (2013.01)

(58) Field of Classification Search
CPC ............... A61F 2/3094; A61F 2/30756; A61B 17/0401; A61B 17/0469
See application file for complete search history.

(56) References Cited

U.S. PATENT DOCUMENTS

| 8,920,497 B2 | 12/2014 | Albertorio et al. |
| 2013/0345749 A1 | 12/2013 | Sullivan et al. |
| 2014/0067061 A1 * | 3/2014 | Kubiak .............. A61B 17/0487 623/13.14 |

* cited by examiner

*Primary Examiner* — Brian A Dukert
(74) *Attorney, Agent, or Firm* — Schwegman Lundberg & Woessner, P.A.

(57) ABSTRACT

A system for installing a labral graft includes placing anchors into a bone thereby immovably coupling the anchors to the bone, coupling a suture to at least one of the anchors, coupling sutures to a graft, using the sutures coupled to the graft to manipulate the graft into position and tightening the sutures, thereby coupling the graft to the bone. Additionally, the system also includes a graft installation funnel having a tapered funnel body and an annular space within the tapered funnel body that is capable of retaining a graft and easing installation of the graft. Further, the system for installing a labral graft includes a graft preparation device including a block with a longitudinal recess, the longitudinal recess having a cross section that mimics the natural shape of a tissue that is to be replaced by a graft, and suture slots.

15 Claims, 4 Drawing Sheets

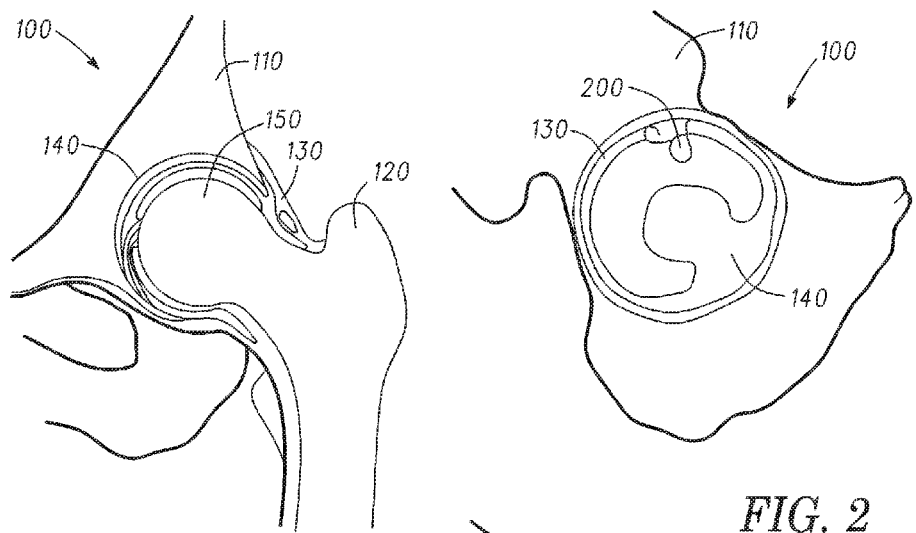
FIG. 1
FIG. 2
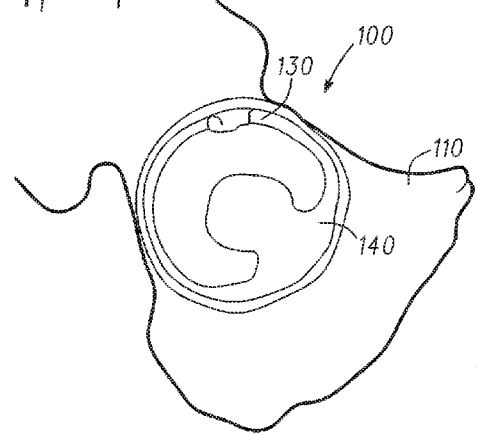
FIG. 3
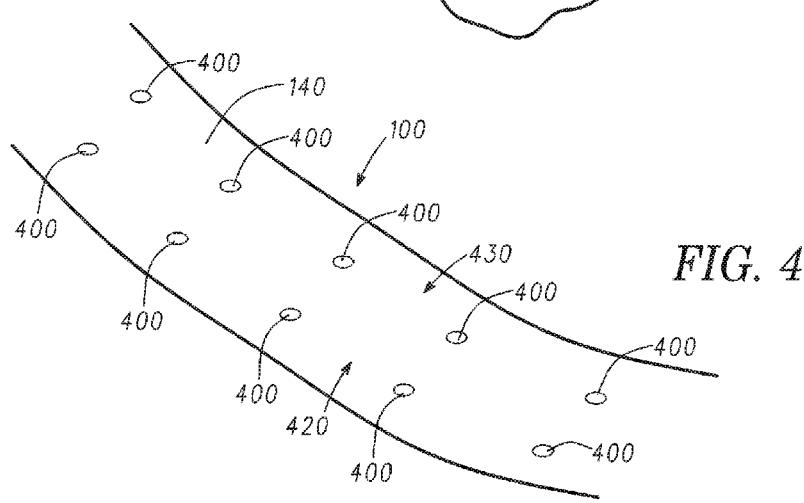
FIG. 4

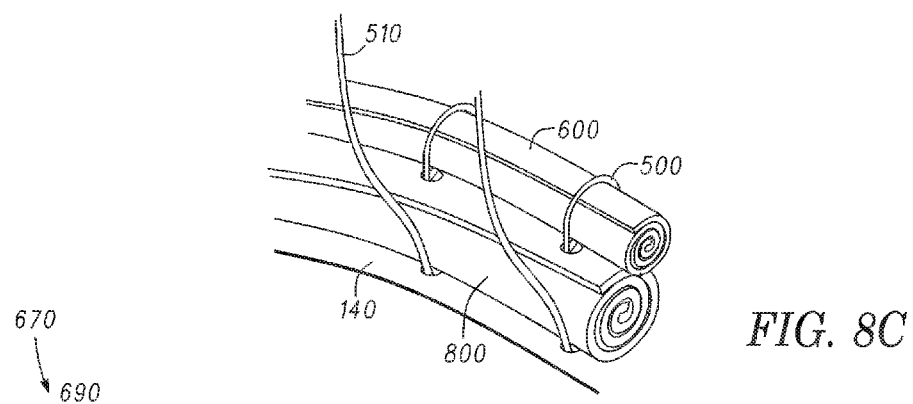
FIG. 8C
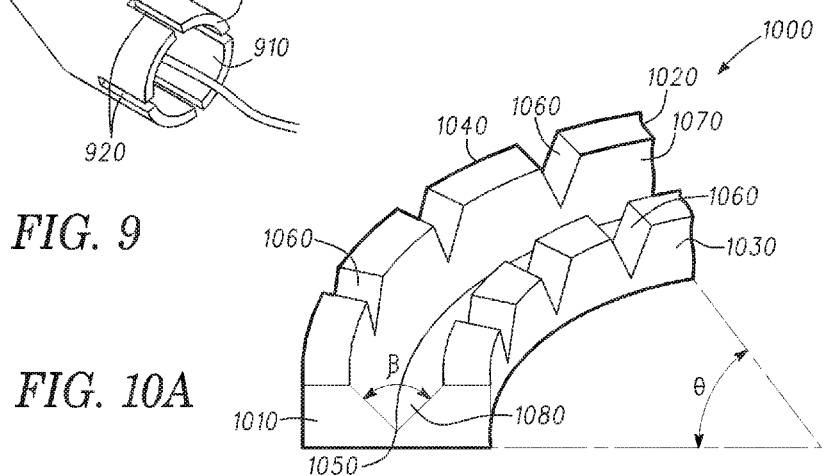
FIG. 9
FIG. 10A
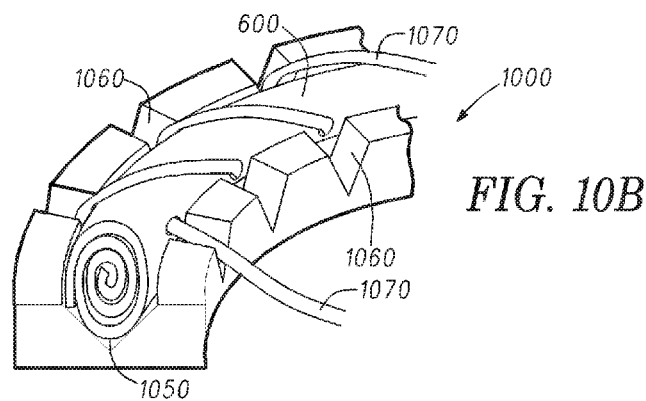
FIG. 10B

LABRAL RECONSTRUCTION SYSTEM AND METHODS

RELATED APPLICATIONS

This application claims the benefit of priority to U.S. Provisional Patent Application No. 62/253,431, filed Nov. 10, 2015, the content of which is hereby incorporated in its entirety.

BACKGROUND

The ball and socket joints of the human body (e.g., hip joint and shoulder joint) have soft tissue (e.g., acetabular labrum or glenoid labrum) affixed to the socket of the ball and socket joint (e.g., the acetabulum or glenoid cavity). This soft tissue can become damaged over time either through genetic defects, normal wear and tear, or through injury (e.g., sports-related injuries, impacts, or falls).

U.S. Pat. No. 8,920,497 B2 refers to a method and instrumentation for acetabular labrum reconstruction. US Pat. Pub. No. 2013/0345749 A1 refers to knotless suture anchors and methods of tissue repair.

OVERVIEW

The present inventors have recognized, among other things, that a problem to be solved can include replacing a portion of a damaged acetabular or glenoidal labrum. The present subject matter can help provide a solution to this problem, such as by providing the correct anatomical shape for a graft, easing installation of the graft, and providing a method to repair the acetabular or glenoidal labrum.

A system for installing a labral graft can include placing anchors into a bone thereby immovably coupling the anchors to the bone, coupling a suture to at least one of the anchors, coupling sutures to a graft, using the sutures coupled to the graft to manipulate the graft into position and tightening the sutures, thereby coupling the graft to the bone. Additionally, the system also can include a graft installation funnel having a tapered funnel body and an annular space within the tapered funnel body that can retain a graft and ease the installation of the graft. Further, the system for installing a labral graft can include a graft preparation device including a block with a longitudinal recess, the longitudinal recess having a cross section that mimics the natural shape of a tissue that is to be replaced by a graft, and suture slots.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIG. 1 is a perspective view of one example of a hip joint.

FIG. 2 is a perspective view of one example of a hip joint with a damaged portion of an acetabular labrum.

FIG. 3 is a perspective view of one example of a hip joint where a damaged portion of an acetabular labrum has been removed.

FIG. 4 is a detailed perspective view of the hip joint of FIG. 3 showing anchors installed in an acetabulum.

FIG. 8C is a detailed perspective view of the hip joint of FIG. 8A, wherein the first and second grafts are coupled to the hip joint.

FIG. 9 is a perspective view of one example of a graft installation funnel.

FIG. 10A is a perspective view of one example of a graft preparation device.

FIG. 10B is a perspective view of one example of a graft within the graft preparation device of FIG. 10A.

DETAILED DESCRIPTION

Figure 5:
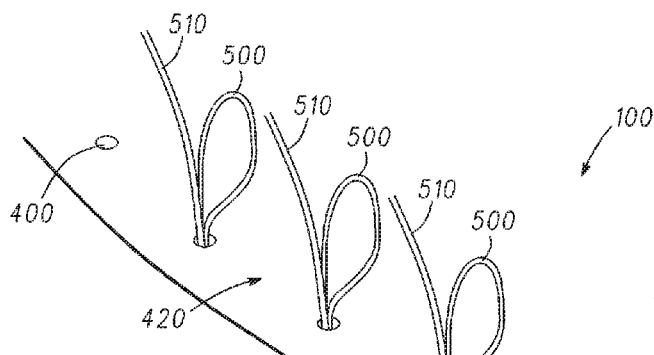
FIG. 5 is a detailed perspective view of one example of a hip joint that has been prepared to receive a first or second graft.

FIG. 1 shows a perspective view of one example of a hip joint 100. The hip joint 100 can include a hip bone 110, a femur 120, and an acetabular labrum 130. The hip bone 110 can include an acetabulum 140. The femur 120 can include a femoral head 150. The acetabulum 140 can be a spherically shaped part of the hip bone 110. The acetabulum 140 can be movably coupled with the femoral head 150. The acetabulum 140 can receive the femoral head 130 and can create the hip joint 100. The hip joint 100 can be a ball-and-socket type of joint. The acetabular labrum 130 can consist of a strip of cartilage or connective tissue that can act as a buffer between the acetabulum 140 and the femoral head 150. The acetabular labrum 130 can reduce wear and tear on the hip joint 100. Additionally, the acetabular labrum 130 can increase the engagement of the femoral head 150 with the acetabulum 140 by providing extra material that can extend a distance from the acetabulum 140, thereby increasing the depth of the socket and providing a more resilient hip joint 100. While the examples described herein are provided in the form of a hip joint, in other examples, the devices and methods described herein are used in other joints, such as a shoulder joint.

FIG. 2 shows a perspective view of one example of a hip joint 100 with a damaged portion of the acetabular labrum 200. The femur 120 is not shown in FIG. 2 for clarity/viewing of the labrum 130. The acetabular labrum 130 can become damaged through accident, injury, or normal usage of the hip joint 110, thereby causing pain or discomfort of varying degrees to an individual. Additionally, the damaged portion of the acetabular labrum 200 can cause no pain whatsoever to the afflicted individual, which can require no remedial action. However, when the pain or discomfort caused by the damaged portion of the acetabular labrum 200 reaches a certain level, reconstruction of the acetabular labrum 130 may be desired to repair the damaged portion of the acetabular labrum 200. Further, more extensive damage to the hip joint 100 can result if no remedial action is taken to repair the damaged portion of the acetabular labrum 200.

FIG. 3 shows a perspective view of one example of a hip joint 100 where a damaged portion of the acetabular labrum 200 has been removed. In an example, the damaged portion of the acetabular labrum 200 can be removed prior to the installation of a graft material to replace the damaged portion of the acetabular labrum 200. The damaged portion of the acetabular labrum 200 can be removed through the usage of scissors, a scalpel, or the like.

FIG. 4 is a detailed perspective view of the hip joint 100 of FIG. 3. In an example, during acetabular labrum reconstruction, the damaged portion of the acetabular labrum 200 can be removed. After the damaged portion of the acetabular labrum 200 has been removed, one or more anchors 400 can be placed into the acetabulum 140 such that the one or more anchors 400 can be immovably coupled to the acetabulum 140. The anchors 400 can be any surgical anchor suitable for use in bone. Alternatively or additionally, the anchors 400 can be knotless anchors configured to securely lock so as to prevent translational sliding of a suture with respect to the knotless anchor.

In one example, a drill and a drill bit can be used to bore a hole in the acetabulum 140 at one or more locations where the damaged portion of the acetabular labrum 200 has been removed. The anchors 400 can be placed in the hole, thereby creating a first row of anchors 420. The anchors 400 can be coupled to the acetabulum 140 through friction, mechanical fastening, epoxies, or the like. In another example the anchors 400 can be sized and shaped such that they can be self-drilling, thereby reducing the amount of labor required to install the anchors 400.

In yet another example, additional anchors 400 can be immovably coupled to the acetabulum 140, such that a second row of anchors 430 can be created. The second row of anchors 430 can be located a distance radially from the first row of anchors 420. In one example, the number of anchors 400 used in the second row of anchors 430 can be equal to the number of anchors 400 used in the first row of anchors 420. It is now appreciated that variations can exist in the number of anchors 400 used in the first row of anchors 420 from the number of anchors 400 in the second row of anchors 430, such as when the needs of a patient dictate that the number of anchors 400 differ between the first and second row of anchors 420, 430. Additionally, the spacing between the anchors 400 of the second row of anchors 430 can be substantially similar to the spacing between the anchors 400 of the first row of anchors 420. The second row of anchors 430 can be offset radially from the first row of anchors 420 a certain distance. The distance between the first row of anchors 420 and the second row of anchors 430 can be dictated by the needs of a patient undergoing the acetabular labrum reconstruction or the geometry of the acetabulum.

In still another example, the number of anchors 400 of the second row of anchors 430 can be less than the number of anchors 400 in the first row of anchors 420. Other anchor spacing and arrangements may be used depending on space constraints or needs of a specific patient.

FIG. 5 is a detailed perspective view of one example of a hip joint 100 that has been prepared to receive a graft. In an example, a loop-shaped suture 500 can be coupled to each of the one or more anchors 400 of the first row of anchors 420 (e.g., one loop-shaped suture 500 can be coupled to one anchor 400, and conversely each anchor 400 only has one loop-shaped suture 500). In an example, the anchor 400 and the loop-shaped suture 500 and the methods for their respective uses can be found in US 2015/0127051 A1 to Kaiser et al., which is incorporated herein by reference. In one example, an end of the loop-shaped suture 500 can be fixed within an anchor 500 with the free end passing through a hook within the anchor 400 to form a loop through which a graft can pass. The loop-shaped suture 500 can have a loop-shaped suture strand 510 that can be pulled so that the loop can be cinched down, such as for securing a first graft (not shown). The loop-shaped suture 500 can be sized and shaped such that the loop-shaped suture 500 can be capable of retaining soft tissue in a specific location when the loop-shaped suture 500 is used in combination with an anchor 400. The loop-shaped suture 500 can have one or more loop-shaped suture strands 510 extending from the loop-shaped suture 500. The one or more loop-shaped suture strands 510 can be manipulated and result in the tightening of the loop-shaped suture 500. The tightening of the loop-shaped suture 500 can retain soft tissue in a specific location.

In another example, a loop-shaped suture 500 can be coupled to each of the anchors 400 (e.g., one loop-shaped suture 500 per anchor 400) of the first row of anchors 420 that are not at the respective ends of the first row of anchors 420. Stated another way, if five anchors 400 can be used in the first row of anchors 420, three loop-shaped sutures 500 would be coupled to the three anchors 400 that are in the middle of the first row of anchors 420, leaving the anchors 400 on the ends of the first row of anchors 420 vacant, In yet another example a loop-shaped suture 500 can be coupled to all but one anchor 400 of the first row of anchors 420. Stated another way, if five anchors 400 are used in the first row of anchors 430, one loop-shaped suture can be coupled to each of the four anchors 400 (e.g., one loop-shaped suture 500 per anchor 400) of the first row of anchors 420, leaving one anchor 500 vacant on an end of the first row of anchors 420.

Figure 6A:
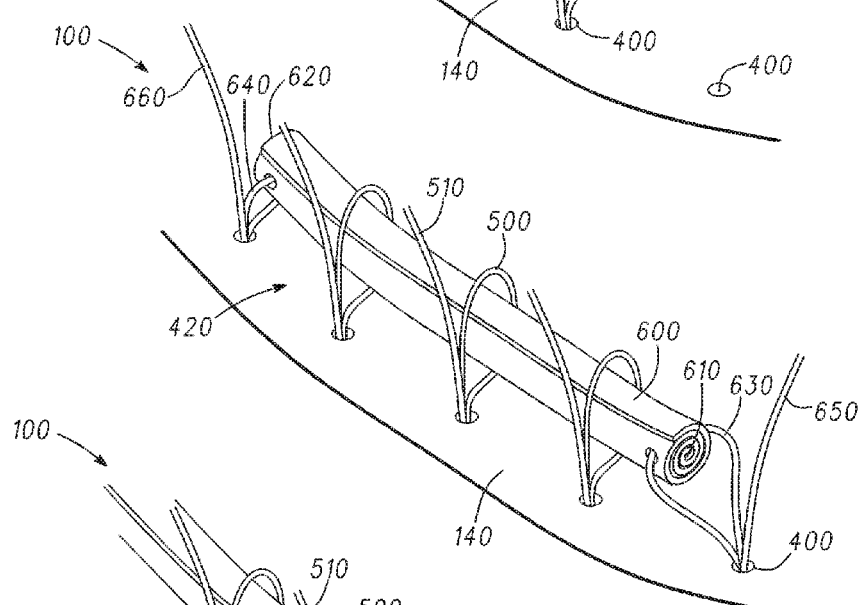
FIG. 6A is a detailed perspective view of one example of a hip joint wherein a first graft has been placed into position within the hip joint.

FIG. 6A is a detailed perspective view of one example of a hip joint 100 wherein a first graft 600 has been placed into position within the hip joint 100. In an example, a material can be harvested from a human cadaver (e.g., dermis or fascia lata) or a xenograft (e.g., bovine or porcine) for use as a first graft 600. In another example, the material can be fabricated through the use of artificial graft material. The material can be rolled, pleated, or shaped, thereby producing the first graft 600 with an initial cross section, an initial shape, a first end of the first graft 610, and a second end of the first graft 620. The initial cross section and the initial shape of the first graft 600 is such that the first graft 600 is of a size and shape similar to the tissue (e.g., the acetabular labrum 130) the first graft 600 is replacing within a living organism (e.g., the damaged portion of the acetabular labrum 200). In yet another example, the material from which the first graft 600 is fabricated may not have an initial cross-section that is similar to the cross section of the tissue that is to be replaced by the first graft 600.

In an example, a human being's acetabular labrum can naturally have a triangular cross section. As described further herein, an individual can manipulate the first graft 600 such that the initial cross section of the first graft 600 is transformed into a triangular cross section. In another example, and as discussed further herein with reference to FIGS. 10A and 10B, the first graft 600 can be fabricated using a graft preparation device having a longitudinal recess with a cross section triangular in shape. The mimicking of the natural shape of the tissue (e.g., the acetabular labrum 130) to be replaced by the first graft 600 can increase the effectiveness and/or resilience of a joint reconstruction procedure, Stated another way, mimicking the natural shape of normal, healthy tissue can result in the first graft 600 performing in a substantially similar manner as normal, healthy tissue (e.g., the acetabular labrum 130). This is in contrast to improperly/sub-optimally/misshaped grafts that do not mimic the natural shape of the normal, healthy tissue (e.g., the acetabular labrum 130), resulting in those grafts not performing in a substantially similar manner as normal, healthy tissue. In one example, the acetabular labrum 130 creates a seal within the hip joint 100. If the first graft 600 does not mimic the natural shape of the acetabular labrum 130, then the first graft 600 may not seal as well as a first graft 600 that mimics the natural shape of the acetabular labrum 130.

In an example, the first graft 600 can be placed near the desired position within the hip joint 100 after placing the anchors 400 within the hip joint 100 and coupling the appropriate number of loop-shaped sutures 500 to the anchors 400. The first graft 600 can have a first end suture 630 coupled to the first end of the first graft 610 and a second end suture 640 coupled to the second end of the first graft 620. The coupling of the first end suture 630 and the second end suture 640 with the first end of the first graft 610 and the second end of the first graft 620, respectively, can result in one or more first end strands 650 extending from the first end of the first graft 610 and one or more second end strands 660 extending from the second end of the first graft 620.

In an example, the first and second end strands 650, 660 can be used to manipulate the first graft 600 into position within the hip joint 100. The first end strands 650 can be fed through each of the loop-shaped sutures 500 coupled to the first row of anchors 420. An individual can then manipulate the first end strands 650, thereby translating the first graft 600 through each of the loop-shaped sutures 500 coupled to the first row of anchors 420. Additionally, the first end strands 650 and the second end strands 660 can be used to couple the first end of the first graft 610 and the second end of the first graft 620, respectively, to the one or more anchors 400 of the first row of anchors 420.

In another example, where there are five anchors 400 in the first row of anchors 420, loop-shaped sutures can be coupled to four of the five anchors 400 of the first row of anchors 420, leaving one anchor vacant on an end of the first row of anchors 420. The loop-shaped suture 500 that is coupled to the anchor on the opposite end of the first row of anchors 420 from the vacant anchor 400 can be fed through the three remaining loop-shaped sutures that are in the middle of the first row of anchors 420 and coupled to the first end of the first graft 610. The coupling of the loop-shaped suture 500 to the first end of the first graft 610 and to the anchor 400 on the end of the first row of anchors 420 can allow for an individual to manipulate the loop-shaped suture strands 510. The manipulation of loop-shaped suture strands 510 on the end of the first row of anchors can result in the loop-shaped suture 500 tightening and thereby translating the first graft 600 through the loop-shaped sutures 500 in the middle of the first row of sutures 420 and then into position within the hip joint 100.

Stated another way, if a loop-shaped suture 500 is located at the end of the first row of anchors 420, regardless of the number of anchors 400 in the first row of anchors 420, the loop-shaped suture 500 located at the end of the first row of anchors 420 can be fed through the other loop-shaped sutures 500 of the first row of anchors 420 and then coupled to the first end of the first graft 610. Alternatively, the loop-shape suture 500 located at the end of the first row of anchors 420 can be coupled to the first end strands 650. The loop-shaped suture strands 510 of the loop-shaped suture 500 located on the end of the first row of anchors 420 can then be manipulated such that the first graft 610 is translated through the other loop-shaped sutures 500 of the first row of anchors 420 and placed into position within the hip joint 100.

Figure 6B:
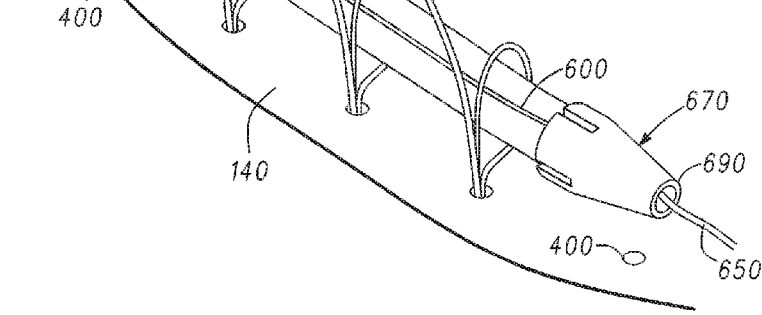
FIG. 6B is a detailed perspective view of one example of a hip joint wherein a first graft has been placed into position with the assistance of a graft installation funnel.

FIG. 6B is a detailed perspective view of one example of a hip joint 100 wherein a first graft 600 has been placed into position with the assistance of a graft installation funnel 670. As discussed further herein with reference to FIG. 9, the graft installation funnel 670 is sized and shaped such that either the first end of the first graft 610 or the second end of the first graft 620 can be inserted into the graft installation funnel 670 such that the first graft 600 is in communication with and is sheathed by the graft installation funnel 670. The graft installation funnel 670 can be used to help ease the translation of the first graft 600 through the loop-shaped sutures 500 that are coupled to the first row of anchors 420. The graft installation funnel 670 can ease translation of the first graft 600 through the loop-shaped sutures 500 by reducing the amount of interference the first graft 600 experiences as it translates through the loop-shaped sutures 500. In other words, the graft installation funnel 670 can provide a narrow tip that more easily fits through the loop-shaped sutures 500.

In an example, the first end suture strands 650 are translated through the second funnel end (not shown in FIG. 6B) of the graft installation funnel 670 and out through the first funnel end 690 of the graft installation funnel 670. The graft installation funnel 670 can then be translated along the first end suture strands 650 such that it can be coupled with the first graft 600. The graft installation funnel 670 can be decoupled from the first graft 600 after the first graft 600 has been translated through the loop-shaped sutures 500 of the first row of anchors 420.

Figure 7:
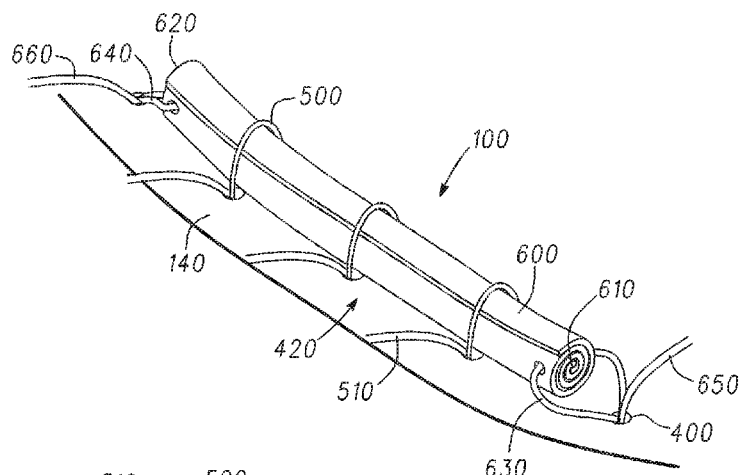
FIG. 7 is a perspective view of an example of a hip joint wherein a first

FIG. 7 is an example of a view of a first graft 600 completely installed within a hip joint 100. In an example, once the first graft 600 has been manipulated into position, the loop-shaped suture strands 510 of the loop-shaped sutures 500 can be manipulated such that the loop-shaped sutures 500 tighten and thereby couple a portion of the first graft 600 to the acetabulum 140. The first end suture 530 and the second end suture 540 can then be coupled to their respective anchors 400.

In another example, the first end suture strands 550 can be coupled to the first row of anchors 420 before the loop-shaped suture strands 510 of the loop-shaped sutures 500 are manipulated, thereby tightening the loop-shaped sutures, and thereby coupling the first end of the graft 610 to the acetabulum 140. After coupling the first end of the graft 610 to the acetabulum 140, the loop-shaped sutures 500 can be tightened in series such that the loop-shaped suture 500 located closest to first end of the graft 610 is tightened first. Then the remaining loop-shaped sutures 500 can be tightened and couple their respective portion of the first graft 600 to the acetabulum 140 based upon which loop-shaped suture is closest into proximity to the first end of the grail 610. Alternatively, the second end sutures 560 can be coupled to an anchor 400 thereby coupling the second end of the graft 620 to the acetabulum 140 first. The loop-shaped sutures 500 can then be tightened in sequence depending upon which loop-shaped suture 500 is closest to the second end of the graft 620. The remaining end of the first graft 600 that remains to be coupled to the acetabulum (either the first or the second end of the graft 610, 620) can then be coupled to the acetabulum.

In one example, the first end suture strands 550, second end suture strands 560, and the loop-shaped suture strands 510 can be trimmed such that they do not irritate or impinge upon the tissue surrounding the area where the first graft 600 is located, once the first graft 600 has been coupled to the acetabulum 140. Alternatively, the first end suture strands 550, second end suture strands 560, and the loop-shaped suture strands 510 can be coupled to corresponding anchors 400 of the second row of anchors 430, thereby retaining the first end suture strands 550, second end suture strands 560, and the loop-shaped suture strands 510 in a position such that they do not irritate or impinge upon the tissue surrounding the area where the first graft 600 is located. The coupling of the first end suture strands 550, second end suture strands 560, and the loop-shaped suture strands 510 can fix the first end suture strands 550, second end suture strands 560, and the loop-shaped suture strands 510 relative to the acetabulum 140.

Figure 8A:
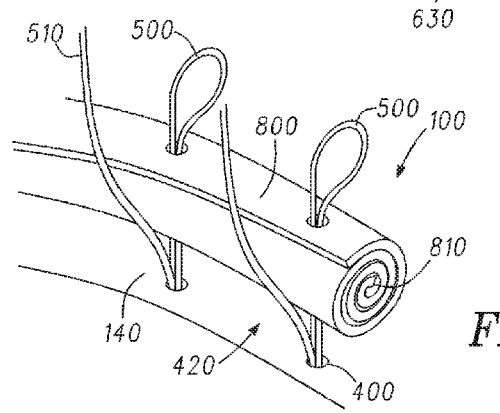
FIG. 8A is a detailed perspective view of one example of a hip joint wherein loop-shaped sutures pierce a second graft prior to the positioning of a first graft.

FIG. 8A is a detailed perspective view of one example of a hip joint wherein loop-shaped sutures 500 pierce a second graft 800 before the first graft 600 (not shown in FIG. 8A) is installed thereon/on top of the second graft 800. The second graft 800 can have a first end of the second graft 810 and a second end of the second graft 820 (not shown). As previously discussed herein, it can be desired to mimic the natural shape of the tissue (e.g., the acetabular labrum 130) that can be replaced by a graft. In one example, wherein it is desired to have a graft mimic the triangular cross section of an acetabular labrum 130, the first graft 600 and the second graft 800 can have a substantially circular cross section and the second graft 800 can have a greater diameter than the first graft 600. The first graft 600 can be stacked on top of the second graft 800, thereby creating a graft with a cross section that mimics the natural shape of the acetabular labrum 130. Stated another way, the stacking of a smaller diameter graft on top of a larger diameter graft can create a triangular cross section. It is now appreciated that one or more grafts can be arranged to create a variety of cross section geometries. In an example, a second graft 800 can be pierced by a needle or the like at locations that correspond to the locations of the anchors 400 of the first row of anchors 420. The previously placed loop-shaped sutures 500 can be translated through the piercings of the second graft 800, thereby placing the second graft into position within the hip joint 100.

Figure 8B:
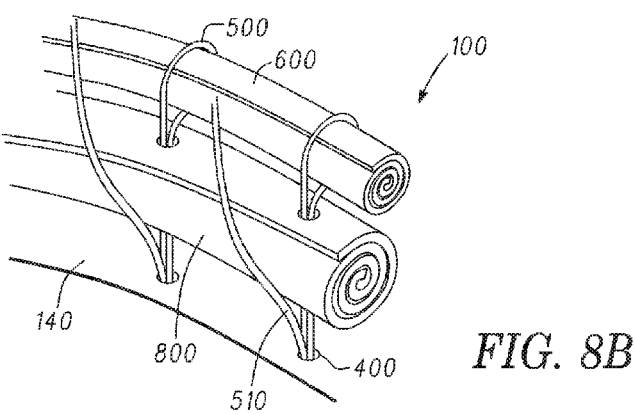
FIG. 8B is a detailed perspective view of the hip joint of FIG. 8A, wherein a first graft is being manipulated into position within the hip joint.

FIG. 8B is a detailed perspective view of the hip joint of FIG. 8A, wherein a first graft 600 is being manipulated into position within a hip joint 100. The first graft 600 can be manipulated into position in the same manner as described previously herein. Alternatively or additionally, the first graft 600 can be manipulated into position with the aid of a graft installation funnel 670, as previously described herein.

FIG. 8C is a detailed perspective view of the hip joint of FIG. 8A, wherein the first and second graft 600, 800 are coupled to a hip joint 100. In an example, the loop-shaped suture strands 510 can be manipulated such that the loop-shaped sutures 500 tighten once the first and second graft 600, 800 have been manipulated into position within the hip joint 100. The tightening of the loop-shaped suture 500 can couple the first and second graft 600, 800 to the acetabulum 140. The coupling of the first and second graft 600, 800 to the acetabulum results in a compound graft (e.g., the stacked combination of the first and second graft 600, 800) that can mimic the natural shape of an acetabular labrum 130.

FIG. 9 is a perspective view of one example of a graft installation funnel 670. In an example, the graft installation funnel 670 can be a tapered funnel body 900 having a first funnel end 690 and a second funnel end 680. The first funnel end 690 can have a diameter less than the second funnel end 680. Stated another way, the graft installation funnel 670 can provide a narrow tip (e.g., the first funnel end 690) that more easily fits through the loop-shaped sutures 500.

Additionally, the graft installation funnel 670 can have an annular space 910 within the tapered funnel body 900. The annular space 910 can be sized and shaped such that the first end of the first graft 610 or the first end of the second graft 810 can be retained within the second funnel end 690 of the tapered funnel body 900. Stated another way, the first end of the first graft 610 or the first end of the second graft 810 can be coupled to the graft installation funnel 670 such that the first end of the first graft 610 or the first end of the second graft 810 is in communication with and is sheathed by the second end of the graft installation funnel 690. It is now appreciated that the second end of the first graft 620 and the second end of the second graft 820 can be used in conjunction with the graft installation funnel 670. The sheathing of the first end of first graft 510 or the first end of the second graft 810 can allow for either the first graft 600 or the second graft 800, respectively, to more easily translate through loop-shaped sutures 500. Stated another way, the graft installation funnel 670 can reduce the amount of interference either the first or second graft 600, 800 experience as the first or second graft 600, 800 translate through the loop-shaped sutures 500.

In another example, the graft installation funnel 670 can have one or more deformation slots 920. The deformation slots 920 can extend a distance longitudinally from the second funnel end 680 toward the first funnel end 690. Additionally, the deformation slots 920 can allow the second funnel end 680 of the graft installation funnel 670 to elastically deform. The elastic deformation of the second funnel end can allow the graft installation funnel to retain a graft (e.g., the first or second graft 600, 800). The retention of a graft (e.g., the first or second graft 600, 800) can result in the coupling of the graft installation funnel with the graft.

In yet another example, the first funnel end 690 can he sized and shaped (such as by including a through-bore or hole) such that either the first end suture strands 550, second end suture strands 560, or the loop-shaped suture 500 (or a combination thereof) can translate through the first funnel end 690 of the tapered funnel body 900. Additionally, the second funnel end 680 can be sized and shaped such that either the first end suture strands 550, second end suture strands 560, or the loop-shaped suture 500 can translate through the second funnel end 680 of the tapered funnel body 900. In still yet another example, a suture can he coupled to the graft installation funnel 670 such that the suture eases the removal of the graft installation funnel 670 from a body (e.g., the graft installation funnel 670 can be decoupled from the first graft 600 and then an individual can use the suture coupled to the graft installation funnel 670 to remove the graft installation funnel 670 from the body).

FIG. 10A is a perspective view of one example of a graft preparation device 1000. In one example, the graft preparation device 1000 can be a block having a first lateral end 1010 and a second lateral end 1020. Additionally, the graft preparation device 1000 can have a first longitudinal side 1030 and a second longitudinal side 1040. The first lateral end 1010 and the second lateral end 1020 can connect the first longitudinal side 1030 and the second longitudinal side 1040. In another example, the graft preparation device 1000 can have a longitudinal recess 1050. The longitudinal recess 1050 can be a recess extending from the first lateral end 1010 to the second lateral end 1020. Additionally, the longitudinal recess 1050 can be located between the first and second longitudinal sides 1030, 1040. Further, the graft preparation device can have first and second longitudinal recess walls 1070, 1080. In yet another example, the first and second longitudinal recess walls 1070, 1080 can be offset from one another at a particular angle (e.g., the angle still yet another example, first and second longitudinal recess walls 1070, 1080 can give the longitudinal recess 1050 a cross section that mimics a natural shape of a tissue that is to be replaced by a graft. Alternatively or additionally, the longitudinal recess 1050 can have a cross section that is circular, triangular, rectangular, or any polygon in shape.

In yet another example, the graft preparation device 1000 can have one or more suture slots 1060. The one or more suture slots 1060 can extend from either the first longitudinal side 1030 or the second longitudinal side 1040. Additionally, the one or more suture slots 1060 can intercept the longitudinal recess 1050. Further, the suture slots can be sized and shaped such that a suture needle or the like can be inserted into the one or more suture slots 1060. In still yet another example, the first lateral end 1010 and the second lateral end 1020 can be offset at a particular angle (e.g., the angle θ) from one another. Alternatively or additionally, the first lateral end 1010 and second lateral end 1020 can be offset at an angle from one another such that the block is curved to substantially correspond to the natural curvature of the acetabular labrum 130. Stated another way, the angle θ can equal the angle necessary to mimic the natural curvature of the acetabular labrum 130.

As previously described herein, in an example, it can be desired to mimic the natural curvature of the tissue (e.g., the acetabular labrum 130) to be replaced by a graft (e.g., the first or second graft 600, 800). The mimicking the natural shape of normal, healthy tissue (e.g., the acetabular labrum 130) by a graft (e.g., the first or second graft 600, 800) can result in the graft (e.g., the first or second graft 600, 800) performing in a substantially similar manner as normal, healthy tissue that is to be replaced by the graft (e.g., the first or second graft 600, 800). The graft preparation device 1000 can assist in fabricating a graft (e.g., the first or second graft 600, 800) that mimics the natural shape of normal, healthy tissue (e.g., the acetabular labrum 130).

FIG. 10B is a perspective view of one example of a graft (e.g., the first or second graft 600, 800) within the graft preparation device 1000 of FIG. 10A. In an example, the graft preparation device 1000 can assist in fabricating a graft because the graft preparation device 1000 can be sized and shaped to mimic the natural curvature and shape of the tissue (e.g., the acetabular labrum 130) to be replaced by the graft (e.g., the first or second graft 600, 800). In another example wherein the graft preparation device mimics the natural shape of an acetabular labrum 130, a graft (e.g., the first or second graft 600, 800) can be placed in the longitudinal recess 1050 of the graft preparation device 1000. The placing of the graft (e.g., the first or second graft 600, 800) within the graft preparation device 1000 can allow the graft (e.g., the first or second graft 600, 800) to mimic the natural curvature of the acetabular labrum 130. The graft (e.g., the first or second graft 600, 800) can then be secured through the use of sutures 1070 or the like, thereby retaining the curvature of the longitudinal recess once the graft (e.g., the first or second graft 600, 800) is removed from the graft preparation device 100. The suture slots 1060 can assist in securing the graft (e.g., the first or second graft 600, 800) by allowing a suture needle, and a suture 1070 coupled thereto, access to the center of graft (e.g., the first or second graft 600, 800) such that the suture needle is able to pierce the graft (e.g., the first or second graft 600, 800), pass through the graft, and out through a corresponding suture slot 1060 on the opposite side of the graft preparation device 1000. The suture needle can be passed through the graft one or more times. The suture 1070 can then be tightened or tied, thereby securing the graft (e.g., the first or second graft 600, 800). The securing of the graft (e.g., the first or second graft 600, 800) can maintain the desired cross section and/or desired shape of the graft.

In another example, it can also be desired to mimic the natural shape of the tissue (e.g., the acetabular labrum 130) that is to be replaced by a graft (e.g., the first or second graft 600, 800). The graft (e.g., the first or second graft 600, 800) can be manipulated such that a force (e.g., applying pressure downward, towards the surface on which the graft preparation device 1000 sits) is applied to the graft (e.g., the first or second graft 600, 800) while it is within the longitudinal recess 1050 of the graft preparation device 1000. The application of force to the graft (e.g., the first or second graft 600, 800) can result in the graft substantially taking on the shape of the longitudinal recess (e.g., the first graft 600 can deform and take on, or mimic, the cross section of the longitudinal recess 1050). The graft (e.g., the first or second graft 600, 800) can then be secured as previously described herein, thereby retaining the shape (e.g., the cross section) of the longitudinal recess 1050.

Various Notes & Examples

Example 1 can include or use a graft preparation device including a block with a first longitudinal side and a second longitudinal side, a first lateral end and second lateral end, connecting the first longitudinal side and the second longitudinal side, a longitudinal recess extending from the first lateral end to the second lateral end between the first and second longitudinal sides, and having a first longitudinal recess wall and a second longitudinal recess wall that give the longitudinal recess a cross section that mimics a natural shape of a tissue that is to be replaced by a graft, and one or more suture slots that are extending from either the first longitudinal side or the second longitudinal side, intercepting the longitudinal recess, and wherein the one or more suture slots are sized and shaped such that a suture needle is capable of being inserted into the one or more suture slots.

Example 2 can include or use, or can optionally be combined with the subject matter of Example 1, to optionally include that the first longitudinal recess wall and the second longitudinal recess wall are offset at a particular angle from one another.

Example 3 can include or use, or can optionally be combined with the subject matter of one or any combination of Examples 1 or 2 to optionally include that the first lateral end and second lateral end are offset at a particular angle from each other such that the block is curved.

Example 4 can include or use, or can optionally be combined with the subject matter of one or any combination of Examples 1 through 3 to optionally include that the first lateral end and second lateral end are offset at an angle from each other such that the block is curved to substantially correspond to the natural curvature of an acetabular labrum.

Example 5 can include or use, or can optionally be combined with the subject matter of one or any combination of Examples 1 through 4 to optionally include that the first lateral end and second lateral end are offset at an angle from each other such that the block is curved to substantially correspond to the natural curvature of a glenoid labrum.

Example 6 can include or use a method for installing a labral graft including placing one or more anchors into a bone such that each of the anchors is immovably coupled to the bone, the anchors creating a first row of anchors, coupling a loop-shaped suture to at least one of the anchors of the first row of anchors, the loop-shaped suture capable of tightening, coupling a first end suture to a first end of a first graft and coupling a second end suture to a second end of the first graft, the first and second end sutures each having one or more strands extending from the first graft, the first and second end sutures used to manipulate the first graft and couple the first end of the first graft and the second end of the first graft to the one or more anchors of the first row of anchors, coupling the first end suture to one of the anchors of the first row of anchors, positioning the first graft, and manipulating one or more strands on an individual loop-shaped suture such that the loop-shaped suture tightens and couples a portion of the first graft to the bone.

Example 7 can include or use, or can optionally be combined with the subject matter of Example 6 to optionally include that coupling the loop-shaped suture to at least one of the anchors of the first row of anchors is performed before placing the at least one anchor into the bone.

Example 8 can include or use, or can optionally be combined with the subject matter of one or any combination of Examples 6 or 7 to optionally include that positioning the first graft includes translating the first graft through individual loop-shaped sutures coupled to the first row of anchors.

Example 9 can include or use, or can optionally be combined with the subject matter of one or any combination of Examples 6 through 8 to optionally include that positioning the first graft includes coupling a loop-shaped suture of the first row of anchors to the first end of the first graft and tightening the loop, thereby translating the first graft into position.

Example 10 can include or use, or can optionally be combined with the subject matter of one or any combination of Examples 6 through 9 to optionally include positioning the first graft includes coupling a loop-shaped suture of the first row of anchors to the first end suture of the first graft and tightening the loop, thereby translating the first graft into position.

Example 11 can include or use, or can optionally be combined with the subject matter of one or any combination of Examples 6 through 10 to optionally include that the first graft is fabricated using a graft preparation device having a longitudinal recess, the longitudinal recess having a cross section that mimics the natural shape of a tissue that is to be replaced by the first graft.

Example 12 can include or use, or can optionally be combined with the subject matter of one or any combination of Examples 6 through 11 to optionally include that a second graft is pierced in locations that correspond to the locations of the anchors of the first row of anchors, translating each of the loop-shaped sutures coupled to the first row of anchors through the corresponding piercings of the second graft, thereby placing the second graft into position within the joint, translating the first graft through each of the loop-shaped sutures coupled to the first row of anchors, thereby locating the first graft in a position on top of the second graft, and manipulating one or more strands on each of the loop-shaped sutures such that the loop-shaped sutures tighten and couple a portion of the first graft and second graft to the bone.

Example 13 can include or use, or can optionally be combined with the subject matter of one or any combination of Examples 6 through 12 to optionally include that one or more anchors are placed in the bone such that the anchors are immovably coupled to the bone, the anchors creating a second row of anchors, the second row of anchors located a radial distance from the first row of anchors.

Example 14 can include or use, or can optionally be combined with the subject matter of Examples 13 to optionally include that the one or more strands of each of the first end suture strands, second end suture strands, and the loop-shaped suture strands is coupled to a corresponding anchor of the second row of anchors such that the one or more strands are fixed relative to the bone.

Example 15 can include or use, or can optionally be combined with the subject matter of one or any combination of Examples 6 through 14 to optionally include that prior to translating the first end of the first graft through individual loop-shaped sutures coupled to the first row of anchors, the first end of the first graft is coupled to a graft installation funnel such that the first end of the first graft is in communication with and is sheathed by an end of the graft installation funnel.

Example 16 can include or use, or can optionally be combined with the subject matter of one or any combination of Examples 6 through 15 to optionally include that after placing the first graft into position within a hip joint, the graft installation funnel is decoupled from the first end of the first graft.

Example 17 can include or use a graft installation funnel including a tapered funnel body having a first funnel end and a second funnel end, an annular space within the tapered funnel body, the annular space sized and shaped such that the annular space is capable of retaining a first end of a graft within the second funnel end of the tapered funnel body and allowing an end suture strand to pass through the second funnel end of the tapered funnel body and out through the first funnel end, and the first funnel end having a diameter less than the second funnel end.

Example 18 can include or use, or can optionally be combined with the subject matter of Example 17 to optionally include that the graft installation funnel has one or more deformation slots, the deformation slots extending a distance longitudinally from the second funnel end toward the first funnel end and allowing the second funnel end of the graft installation funnel to elastically deform.

Example 19 can include or use a method for fabricating a labral graft including manipulating a material to produce a graft with an initial cross section and initial shape, positioning the first graft in a graft preparation device, and applying a force to the graft within the graft preparation device, thereby creating a desired cross section for the graft.

Example 20 can include or use, or can optionally be combined with the subject matter of Example 19 to optionally include that the graft is pierced at one or more suture slots of the graft preparation device and then securing the graft, thereby maintaining the desired cross section and desired shape of the graft.

Example 21 can include or use a method for installing a labral graft, including placing one or more anchors into a bone such that each of the anchors is immovably coupled to the bone, the anchors creating a first row of anchors, coupling anchor sutures to at least one of the anchors, coupling a first end suture to a first end of the graft and coupling a second end suture to a second end of the graft, the first and second end sutures used to manipulate the graft and couple the first and second end of the graft to the one or more anchors of the first row of anchors, coupling the first end suture to one of the first row of anchors, positioning the graft, and manipulating the one or more anchor sutures such that the sutures tighten and couple a portion of the graft to the bone.

Each of these non-limiting examples can stand on its own, or can be combined in various permutations or combinations with one or more of the other examples.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. A graft preparation device comprising:
   a block having:
   a first longitudinal side and a second longitudinal side;
   a first lateral end and second lateral end, connecting the first longitudinal side and the second longitudinal side;
   a longitudinal recess having an opening and a base, the longitudinal recess extending from the first lateral end to the second lateral end between the first and second longitudinal sides, and having a first longitudinal recess wall and a second longitudinal recess wall that give the longitudinal recess a cross section that mimics a natural shape of a tissue that is to be replaced by a graft, wherein the first and second longitudinal walls are spaced apart from each other at the opening of the longitudinal recess and converge to form the base of the longitudinal recess; and
   one or more suture slots:
   extending from either the first longitudinal side or the second longitudinal side;
   intercepting the longitudinal recess; and
   wherein the one or more suture slots are sized and shaped such that a suture needle is capable of being inserted into the one or more suture slots.

2. The graft preparation device of claim 1, wherein the first longitudinal recess wall and the second longitudinal recess wall are offset at a particular angle from one another.

3. The graft preparation device of claim 1, wherein the first lateral end and second lateral end are offset at a particular angle from each other such that the block is curved.

4. The graft preparation device of claim 1, wherein the first lateral end and second lateral end are offset at an angle from each other such that the block is curved to substantially correspond to a natural curvature of an acetabular labrum.

5. The graft preparation device of claim 1, wherein the first lateral end and second lateral end are offset at an angle from each other such that the block is curved to substantially correspond to a natural curvature of a glenoid labrum.

6. A graft preparation device comprising:
   a block having:
   a first longitudinal side and a second longitudinal side;
   a first lateral end and second lateral end, connecting the first longitudinal side and the second longitudinal side;
   a longitudinal recess having an opening and a base extending from the first lateral end to the second lateral end between the first and second longitudinal sides, and having a first longitudinal recess wall and a second longitudinal recess wall that give the longitudinal recess a cross section that mimics a natural shape of a tissue that is to be replaced by a graft, and wherein the first and second longitudinal recess walls are offset at a predetermined angle from one another to be spaced apart at the opening of the longitudinal recess and converge towards one another to form the base of the longitudinal recess; and
   a plurality of suture slots sized and shaped such that a suture needle is capable of being inserted therein, wherein the plurality of suture slots are arranged in one or both of the first longitudinal side or the second longitudinal side and communicate with the longitudinal recess.

7. The graft preparation device of claim 6, wherein the first lateral end and second lateral end are offset at a particular angle from each other such that the block is curved.

8. The graft preparation device of claim 6, wherein the first lateral end and second lateral end are offset at an angle from each other such that the block is curved to substantially correspond to a natural curvature of an acetabular labrum.

9. The graft preparation device of claim 6, wherein the first lateral end and second lateral end are offset at an angle from each other such that the block is curved to substantially correspond to a natural curvature of a glenoid labrum.

10. The graft preparation device of claim 6, wherein the longitudinal recess has a cross section that is one of circular, triangular, rectangular, or any polygon in shape.

11. A graft preparation device comprising:
a block having:
a first longitudinal side and a second longitudinal side;
a first lateral end and second lateral end, connecting the first longitudinal side and the second longitudinal side, wherein the first lateral end and second lateral end are offset at an angle from each other such that the block is curved to substantially correspond to a natural curvature of tissue of a patient;
a longitudinal recess having an opening and a base, the longitudinal recess extending from the first lateral end to the second lateral end between the first and second longitudinal sides, and having a first longitudinal recess wall and a second longitudinal recess wall that give the longitudinal recess a cross section that mimics a natural shape of a tissue that is to be replaced by a graft, and wherein the first and second longitudinal recess walls are spaced apart at the opening of the longitudinal recess and converge towards one another to form the base of the longitudinal recess; and
a plurality of suture slots sized and shaped such that a suture needle is capable of being inserted therein, wherein the plurality of suture slots are arranged in one or both of the first longitudinal side or the second longitudinal side and communicate with the longitudinal recess.

12. The graft preparation device of claim 11, wherein the first longitudinal recess wall and the second longitudinal recess wall are offset at a predetermined angle from one another.

13. The graft preparation device of claim 11, wherein the tissue comprises one of a glenoid labrum or a acetabular labrum.

14. The graft preparation device of claim 11, wherein the longitudinal recess has a cross section that is one of circular, triangular, rectangular, or any polygon in shape.

15. The graft preparation device of claim 1, wherein the longitudinal recess has a cross section that is one of circular, triangular, rectangular, or any polygon in shape.

* * * * *